United States Patent [19]

Jones et al.

[11] 4,452,774

[45] Jun. 5, 1984

[54] ISONITRILE RADIONUCLIDE COMPLEXES FOR LABELLING AND IMAGING AGENTS

[75] Inventors: Alun G. Jones, Newton Centre; Alan Davison, Needham; Michael J. Abrams, Allston, all of Mass.

[73] Assignees: President and Fellows of Harvard College; Massachusetts Institute of Technology, both of Cambridge, Mass.

[21] Appl. No.: 373,511

[22] Filed: Apr. 30, 1982

[51] Int. Cl.³ .................. A61K 43/00; A61K 49/00; C07F 1/08; C07C 121/20

[52] U.S. Cl. .................. 424/1.1; 260/429 R; 260/438.5 R; 260/439 R; 260/440; 260/464; 260/465 R; 260/465 G; 260/465.8 R

[58] Field of Search .................. 424/1, 1.5, 9; 260/429 R, 440, 446, 464, 465 R, 465 G, 465.8 R, 438.1, 438.5, 439; 568/2, 8, 13–17

[56] References Cited

U.S. PATENT DOCUMENTS

| 4,017,596 | 4/1977 | Loberg et al. | 260/429 R |
| 4,197,312 | 4/1980 | Sloboda et al. | 260/429 R |
| 4,338,248 | 7/1982 | Yokoyama et al. | 424/1 |
| 4,363,793 | 12/1982 | Blau et al. | 424/1 |

OTHER PUBLICATIONS

Wistow, Brian W. et al., *Clinical Sciences*, Investigative Nuclear Medicine, vol. 19, (No. 5): 483–487 (1978).

Szalda, David J. et al., *Inorganic Chemistry*, 20:3851–3857 (1981).

Mialki, William S. et al., *Inorganic Chemistry*, 21:480–485 (1982).

Doonan, Daniel J. et al., *Inorganic Chemistry*, vol. 13 (No. 4) (1974).

Kassis, A. I. et al., *The Journal of Nuclear Medicine*, 21:88–90 (1980).

Deutsch, Edward et al., *Science*, vol. 214:85–86 (1981).

Deutsch, Edward et al., *The Journal of Nuclear Medicine*, 22:897–907 (1981).

Smith, T. D. et al., *The Journal of Nuclear Medicine*, vol. 17 (No. 2): 126–132 (1975).

Davison et al., *Inorg. Chem.* 20 (No. 6): 1629–1632 (1981).

Jones et al., *J. Nuclear Med.* 21 (No. 3): 279–281 (1980).

Treichel et al., *Inorg. Chem.* 16 (No. 5): 1167–1169 (1977).

*Primary Examiner*—Christine M. Nucker
*Attorney, Agent, or Firm*—Sewall P. Bronstein; George W. Neuner

[57] ABSTRACT

A coordination complex of an isonitrile ligand and radionuclide such as Tc, Ru, Co, Pt, Fe, Os, Ir, W, Re, Cr, Mo, Mn, Ni, Rh, Pd, Nb and Ta, is useful as a diagnostic agent for labelling liposomes or vesicles, and selected living cells containing lipid membranes, such as blood clots, myocardial tissue, gall bladder tissue, etc.

36 Claims, No Drawings

ISONITRILE RADIONUCLIDE COMPLEXES FOR LABELLING AND IMAGING AGENTS

This invention was made with Government support and the U.S. Government has certain rights in the invention.

This invention relates to novel isonitrile complexes of radionuclides, i.e., for example, of radioactive isotopes such as, but not limited to, $^{99m}Tc$, $^{99}Tc$, $^{97}Ru$, $^{51}Cr$, $^{57}Co$, $^{188}Re$, and $^{191}Os$. The complexes can readily be prepared and isolated at both marco and tracer concentrations in aqueous media, together with any of a wide variety of counterions, as appropriate. They display remarkable effective labelling characteristics for liposomes or vesicles, and a variety of living cells containing lipid membranes, and are also effective imaging agents for detecting abnormalities in the tissues of various organs as well as the existence of blood clots. The complexes of $^{99m}Tc$ are particularly preferred because of the desirable nuclear properties of this radiosotope, i.e., its half-life and gamma ray energy.

A variety of radioisotope imaging and labelling agents have been developed in the past; however, the complexes previously available have generally suffered from the shortcomings of high cost, complexity of the method of preparation, or failure to exhibit high quality imaging or highly effective labelling because of insufficient lipophilic properties.

Isonitrile complexes of various non-radioactive metals have been described but there has been no suggestion that isonitrile complexes of radionuclides would have properties making them desirable or useful as imaging or labelling agents. Oxine complexes of $^{99m}Tc$ have been described for use in labelling platelets. Wistow et al., J. Nucl, Med., Vol. 19, 483–487 (1978). The direct labelling of red blood cells with $^{99m}Tc$ by a reductive process, and the use of the labelled cells for imaging have been described. Smith et al., J.Nucl.Med., Vol. 17, 126–132 (1976). Various complexes of $^{99m}Tc$ with arsenic- and phosphorus-containing organic compounds have been proposed for use as imaging and labelling agents. Deutsch et al., Science, Vol. 214, 85–86 (1981); J.Nucl.Med., Vol. 22, 897–907 (1981); European Pat. Appln. No. 81400618.5, published Oct. 28, 1981, Publn. No. 0038756.

Because of the general availability of supplies of $^{99m}Tc$ in clinical laboratories in the form of pertechnetate as well as the desirable half-life and gamma ray energy of this radionuclide, the complexes of the present invention preferably contain $^{99m}Tc$, although complexes with other radionuclides are also embraced within the broad scope of the invention as stated above. Moreover, the general availability of supplies of pertechnetate make it convenient to use kits for preparation of various complexes of $^{99m}Tc$.

The present invention consequently comprises a coordination complex of an isonitrile ligand with a radioactive metal (radionuclide) selected from the class consisting of radioactive isotopes of Tc, Ru, Co, Pt, Fe, Os, Ir, W, Re, Cr, Mo, Mn, Ni, Rh, Pd, Nb, and Ta, and methods for using such complexes. Preferably, isonitrile complexes of this invention comprise one of the above radioactive metals wherein each available coordination site is filled with an isonitrile ligand. The isonitrile ligand can be either monodentate or polydentate such as, for example, bidentate or tridentate. The invention further comprises a kit for converting a supply of a radionuclide, e.g. $^{99m}Tc$-pertechnetate to a complex as stated above, said kit comprising an isonitrile ligand and a reducing agent capable of reducing the radioactive metal to form the coordination complex.

For purposes of this invention, useful radionuclides are radioactive metals having decay properties that are amenable for use as a tracer.

In accord with one embodiment of the present invention complexes can be represented by the formula:

$$[A((CN)_xR)_yB_zB'_{z'}]^n$$

in which A is a radionuclide selected from radioactive isotopes of Tc, Ru, Co, Pt, Fe, Os, Ir, W, Re, Cr, Mo, Mn, Ni, Rh, Pd, Nb, and Ta, for example, $^{99m}Tc$, $^{99}Tc$, $^{97}Ru$, $^{51}Cr$, $^{57}Co$, $^{188}Re$ and $^{191}Os$; $(CN)_xR$ is a monodentate or polydentate isonitrile ligand bonded to the radionuclide through the carbon atom of the CN group; R is an organic radical; B and B' are independently selected from other ligands well known to those skilled in the art that result in isonitrile complexes, including solvents such as water, chloro and bromo groups, and ligands comprising one or more neutral donor atoms capable of forming bonds with said radionuclide; x and y are each independently, integers from 1 to 8; z and z' are each independently 0 or an integer from 1 to 7; with the proviso that $(xy)+z+z'$ is less than or equal to 8; and n indicates the charge of the complex and can be 0 (neutral), or a positive or negative integer the value of which depends upon the valence state of A, and the charges on R, B and B'. Any desired counterion can be present as required by the charge on the complex with the proviso that such counterion must be pharmaceutically acceptable if the complex is to be used in vivo.

In the above formula, R is an organic radical that can have additional neutral donor atoms capable of forming coordinate bonds with the radionuclides. If such additional donor atom(s) are used, the number of such donor atoms(s) should be added to x to determine z and z' within the aforementioned constraint that $(xy)+z+z'$ are less than or equal to 8.

A neutral donor atom is defined as an atom having a free-election pair available for accepting a proton to provide a charged ligand or for complexing with a radionuclide to form a coordination complex. Examples of neutral donor atoms suitable for use in this invention include, for example, arsenic, phosphorus, nitrogen, sulfur, oxygen, selenium, tellurium, and the like.

Although complexes of this invention can be neutral, or positively or negatively charged, the class of lipophilic cationic complexes is presently preferred.

Any desired counterion may also be present in the compostion, such as, in the case of cationic complexes, chloride, fluoride, bromide, iodide, hydroxide, sulfate or bisulfate, dihydrogen phosphate, fluoroborate, hexafluorophosphate, etc. Depending upon the particular radionuclide, the valence state and other conditions for complexing, a particular radioactive metal can have from one to eight isonitrile ligands bonded thereto. As aforesaid, each isonitrile ligand is bonded to the radionuclide through the isonitrile carbon atom. Preferably, the complexes of this invention are kinetically inert, and hence stable products. However, the complexes need only be sufficiently stable for the intended use.

The organic radical R can be aliphatic or aromatic and may be substituted with a variety of groups which may or may not be charged. When the organic radical R carries a charged substituent group, the charge on the resultant complex is the summation of the charges of the ligands (R, B and B') and the charge of the radionuclide. Among the aromatic R groups which may be present are phenyl, tolyl, xylyl, naphthyl, diphenyl and substituted aromatic groups containing such substituents as halo, e.g., chloro, bromo, iodo or fluoro; hydroxy, nitro, alkyl, alkoxy, etc.; among the aliphatic R groups which may be present are alkyl, preferably containing 1 to 20 carbon atoms, such as methyl, ethyl, n-propyl, isopropyl, n-butyl, isobutyl, n-hexyl, 2-ethylhexyl, dodecyl, stearyl, etc. Substituent groups may also be present in the aliphatic groups, including among others the same substituent groups as those listed above for aromatic groups.

When the isonitrile ligand is a polydentate ligand such as, for example, a bidentate ligand having the structure CNRNC, the organic radical portion of the ligand can be the same as defined for R above. In such case the number of isonitrile ligands required for each complex is appropriately reduced.

In general, because the desired lipophilic characteristics in the complex can be achieved without the need for substituent groups, it is preferred for the sake of simplicity to employ unsubstituted hydrocarbon groups as the R groups. However, the lipophilic characteristics of the complex can be further varied by varying the R groups to adapt the complex for labelling selected materials, for membrane transport such as for the blood-brain barrier, or for imaging selected organs and dynamic processes related to their function.

In another embodiment, the complex of the present invention is a homoleptic six coordinate (hexakis) cationic complex having the formula $$[A(CNR)_6]^+$$

in which A is a monovalent radionuclide selected from technetium, or $^{188}Re$, CNR is a monodentate isonitrile ligand, and R is an organic radical as defined above. A suitable counterion such as described above is also present.

The complexes of the present invention can easily be prepared by admixing a salt of the radioactive metal and the isonitrile ligand in the presence of a suitable reducing agent, if required, in aqueous media at temperatures from room temperature to reflux temperature or even higher, and are obtained and isolatable in high yield at both macro (carrier added, e.g. $^{99}Tc$) concentrations and at tracer (no carrier added, e.g. $^{99m}Tc$) concentrations of less than $10^{-6}$ molar. In some cases the isonitrile ligand can itself act as the reducing agent thus eliminating the need for an additional reducing agent. Suitable additional reducing agents, when required or desired are well known to those skilled in the art. The reaction is generally complete after 5 minutes to 2 hours, depending upon the identity of the particular reagents employed. The radiolabelled complex is made in the same way as the corresponding non-radioactive isonitrile complex by simply substituting the desired radionuclide for the corresponding non-radioactive element in the starting materials, except in the case of technetium because all technetium isotopes are radioactive.

In the case of technetium such as, for example $^{99}Tc$ or $^{99m}Tc$, a complex in accord with this invention is preferably made by mixing pertechnetate ($Tc^{-7}$) with the desired isonitrile in aqueous medium, then adding to the reaction mixture an appropriate reducing agent capable of reducing the technetium. Among suitable reducing agents are alkali metal dithionites, stannous salts, sodium borohydride, and others, as is well known.

The isonitrile technetium complexes of this invention can also be prepared from preformed technetium complexes having oxidation states for technetium of, for instance, +3, +4 or +5, by treating these preformed complexes with an excess of isonitrile ligands under suitable conditions. For example, the technetium-isonitrile complex can also be prepared by reacting the desired isonitrile ligand with the hexakis-thiourea complex of $Tc^{+3}$ or with a technetium-glucoheptonate complex, or the like.

An excess of the isonitrile ligand, up to 50 to 100% molar excess or more, and an excess of reducing agent, can be used in the complexing reaction to ensure maximum yield from the technetium. Following the reaction, the desired complex can be separated from the reaction mixture, if required, by crystallization or precipitation or by conventional chromatography or ion exchange chromatography.

The following specific examples are intended to illustrate more fully the nature of the present invention without acting as a limitation upon its scope.

EXAMPLE 1

Preparation of hexakis-(t-butylisonitrile) technetium (I) hexflurophosphate from $[Tc(III) (tu)_6]^{3+}$ where tu=thiourea To a 500 ml round bottom flask were added a stir bar, 0.84 g of $[^{99}Tc(thiourea)_6]Cl_3$ (0.13 mmol), methanol (25 ml) and 0.1 g t-butylisonitrile (1.3 mmol). The stirred reaction mixture was refluxed for 1.5 hr., and the resulting pale yellow solution transferred to a 100 ml beaker and water (40 ml) added. The volume was reduced to half by stirring and heating on a hot plate. Then 30 ml water was added and the volume reduced to a half as before.

The almost colorless solution was cooled to room temperature and 0.5g $[NH_4][PF_6]$ in water (10 ml) added, precipitating a white solid which was collected by suction filtration. This was washed with water (10 ml) and ether (10 ml) and dried in vacuo.

Yield of $[(t-C_4H_9NC)_6{}^{99}Tc][PF_6]$ 0.06g (0.08 mmol) equivalent to 62% based on Tc. MP=222° C.

The complex is soluble in polar organic solvents and was recrystallized by slow evaporation from an acetone/water solution (4:1 v/v) giving white crystals. Analysis for $C_{30}H_{54}F_6N_6PTc$

|  | C | H | N |
|---|---|---|---|
| Calc. (%) | 48.50 | 7.34 | 11.32 |
| found | 48.60 | 7.25 | 11.32 |

Optical spectrum (in $CH_3CN$)
  260 nm (shoulder)
  235 nm
  $\epsilon = 8 \times 10^4$ cm$^{-1}$mol$^{-1}$]
Infrared (KBr)
  $\nu(CN) = 2080$ cm$^{-1}$ (strong)
Conductivity ($CH_3CN$; $10^{-3}M$)
  $\Lambda = 140$ ohm$^{-1}$cm$^2$mol$^{-1}$
Field desorption mass spectometry (positive ion mode)
  m/z=597 (cation, C+)

EXAMPLES 2-6

Standard preparation of [(RNC)$_6$Tc]$^+$ cations at carrier added levels

Where

R=—CH$_3$,—n—C$_3$H$_7$,—i—C$_3$H$_7$,—C(CH$_3$)$_3$,—cyclohexyl, —methyl, —n—propyl, —isopropyl, —tertiary butyl.

To a 50 ml round-bottomed flask was added ethanol (10ml), water (10 ml, pH adjusted to 12 with NaOH), 2.5 ml RNC, 0.7 ml of 0.438 M ammonium pertechnetate (NH$_4$)]$^{99T}$cO$_4$], and a stir bar. Sometimes, for convenience of analysis, the $^{99m}$Tc isotope was used as a tracer. A second solution containing 0.21 g sodium dithionite (Na$_2$S$_2$O$_4$) in water (5 ml, pH 12) was prepared, and added dropwise to the first reaction mixture. The solution was brought to reflux using a heating mantle, and maintained for 15 minutes. A further 50 mg Na$_2$S$_2$O$_4$ solution were then added dropwise and the solution refluxed for a further 30 minutes.

The reaction mixture was transferred to a 100 ml beaker and the volume reduced to a half by boiling off solvent on a hot plate. Water (40 ml) was added and the solution cooled to room temperature. 0.5 g of [NH$_4$][PF$_6$] in water (10 ml) was added, immediately, precipitating a white solid. This was collected by vacuum filtration, washed with water (10 ml) and ether (10 ml), and subsequently dried in vacuo.

Recrystallization from acetone/water yields white crystalline [Tc(CNR)$_6$][PF$_6$] in approximately 90% yield with respect to technetium.

EXAMPLES 7-8

Tracer (no carrier added) synthesis of [Tc(CNC(CH$_3$)$_3$)$_6$]$^+$ hexakis-(t-butylisonitrile) technetium (I) cation

1. By sodium dithionite reduction

In a standard scintillation counting vial were mixed isotonic saline (2 ml) containing $^{99m}$TcO$_4$- obtained by elution of a $^{99}$Mo/$^{99m}$Tc radionuclide generator, 2 drops of 1N NaOH solution, ethanol (2 ml), and a small stirring bar. Then, 65µl of t-butylisonitrile were added. A second solution of 20 mg sodium dithionite (Na$_2$S$_2$O$_4$) freshly dissolved in water (pH adjusted to 12 with NaOH) was prepared and this solution added to the first.

The mixture was stirred for 15 minutes and then transferred to a siliconized 50 ml round bottomed flask fitted with a vacuum adaptor. Solvent was removed in vacuo using heat from an infra-red lamp. The residue was washed with ethanol (100 µl) and then with isotonic saline (1 ml). This solution then contained the isonitrile complex in a form suitable for administration to animals. The product of reaction was analyzed by HPLC (high pressure liquid chromatography) before use.

2. By sodium glucoheptonate reduction

A commercially available stannous glucoheptonate radiopharmaceutical kit (Glucosan $^{TM}$, New England Nuclear Corporation) was reconstituted using isotonic saline (5 ml). The resulting solution was withdrawn using a syringe and added to 2 mg SnCl$_2$.2H$_2$O in a scintillation vial. The mixture was stirred for five minutes, and 1 ml withdrawn and added to a siliconized Vacutainer $^{TM}$ tube containing t-butylisonitrile (20 µl), ethanol (120 µl), and a small stirring bar. The mixture was stirred for several minutes and then filtered through a 0.22 µm Millipore filter into a second siliconized tube.

To the resulting clear solution was added isotonic saline (0.5 ml) containing an appropriate level of $^{99m}$TcO$_4$- obtained by eluting a commercial radionuclide generator. The solution was stirred for five minutes.

Extraction of the product

This step may be used with either of the above syntheses to provide a pure sample of the isonitrile complex freed from the other materials in the syntheses.

The solution was transferred to a separatory funnel (50 ml) and twice extracted with methylene chloride (3 ml). The organic phase was twice washed with isotonic saline (5 ml) and then transferred to a siliconized round-bottomed flask (50 ml) fitted with a vacuum adaptor. The solvent was removed in vacuo, aided by heating with an infra-red lamp. The flask was washed first by addition of ethanol (100 µl) followed by saline (1 ml). The solution was then ready for administration to animals after assay by HPLC, the complex being in the form of a solution in a physiologically acceptable nontoxic carrier.

Both procedures can be used to prepare the other complexes of the invention. Those prepared include methyl, n-propyl, isopropyl, n-butyl, tert-butyl, and cyclohexyl isonitrile complexes of $^{99m}$Tc.

Kits in accord with the present invention comprise a quantity of a reducing agent for reducing a preselected radionuclide. Preferably, such kits contain a predetermined quantity of an isonitrile ligand and a predetermined quantity of a reducing agent capable of reducing a predetermined quantity of a preselected radionuclide. It is also preferred that the isonitrile ligand and reducing agent be lyophilized to facilitate storage stability. The isonitrile ligand and reducing agent can be contained in a sealed, sterilized container.

In one embodiment of the invention, a kit for use in making the complexes of the present invention from a supply of $^{99m}$Tc such as the pertechnetate solution in isotonic saline available in most clinical laboratories includes the desired quantity of a selected isonitrile ligand to react with a selected quantity of pertechnetate, and a reducing agent such as sodium dithionite in an amount sufficient to reduce the selected quantity of pertechnetate to form the desired complex.

Injection of the t-butyl isonitrile products of Examples 7 and 8 into animal models followed by conventional imaging procedures showed that vascular emboli can be detected in the lungs as well as in other parts of the vasculature, as described below. Following the detection by gamma camera of unidentified sites of localization in the lung field of apparently normal, healthy dogs, the fact that these represented blood clots was determined. Autologous clots prepared in vitro and labeled with small amount of $^{99m}$Tc-sulfur colloid were introduced into the lung of a dog and their position determined by scanning. A large (several mCi) dose of $^{99m}$Tc-hexakis-(tertiary-butyl-isonitrile) technetium (I) was injected and several of the clots were subsequently visualized. Computer analysis of the data collected showed conclusively that localization was occurring. Furthermore, analysis of the initial perfusion phase in the lung showed areas of deficit in blood flow associated with several of the emboli. Other experiments yielded similar results.

In other experiments isonitrile complexes of this invention were used to label liposomes; to label mammalian cells such as Chinese hamster V-79 lung fibrolast cells, leukocytes isolated from rabbit blood, and human erythrocytes (red blood cells); to visualize bone marrow; to measure lung function; and for mycardial imaging. For instance, both tertiary-butyl and isopropyl isonitrile products have been used to visualize myocardial tissue by external imaging.

Such cells and liposomes can be readily labeled by incubating the radiolabeled complexes of this invention with such cells or liposomes in a suitable medium and measuring the uptake of radioactivity in accord with the methods described by Kassis, A.I. et al., *J. Nucl. Med.*, Vol. 21, 88–90 (1980). Incorporation of the radioactive complex can be as high as 29 pCi/cell. Studies have shown that the radioactive label can be 90% retained for up to sixteen hours. Autologous leukocytes separated from fresh rabbit blood were labeled with the $^{99m}$Tc complex and subsequently reinjected into the rabbit. The distribution of the radiolabeled cells could be followed by gamma camera. Also liposomes have been labeled by similar techniques and their distribution in mice followed by a gamma camera.

Thus, it can be readily appreciated that complexes of this invention are useful not only in visualizing cardiac tissue, but also in detecting the presence of thrombi in the lung and associated areas of blood perfusion deficits, for studying lung function, for studying renal excretion, and for imaging bone marrow and the hepatobiliary system. The complexes are further useful for radioactive tagging of cells and formed elements of blood, other animal cells, plant cells, and small organisms which possess membranous exteriors, e.g., single-cell entities, microbes, etc. In addition, they can be employed to label previously prepared liposomes without the necessity for encapsulation as is the case with many other labelling agents. Finally, complexes of the inventors can be employed thereapeutically.

The choice of radionuclides will depend on the use. For example, preferred radionuclides for diagnostic imaging are radioactive isotopes of Tc, Ru, Co, Pt, Fe, Os, and Ir; preferred radionuclides for therapeutic uses are radioactive isotopes of W, Re, Fe, and Os; preferred radionuclides for radioactive tagging are Cr, Mo, Co, Tc, Fe, Mn, W, Ru, Ni, Rh, Ir, Pd, Nb, and Ta.

This invention has been described in detail including the preferred embodiments thereof. However, it will be appreciated that those skilled in the art, upon consideration of this disclosure, may make modifications and improvements within the spirit and scope of this invention.

We claim:

1. A coordination complex of an isonitrile ligand and a radioactive metal selected from the class consisting of radioactive isotopes of Tc, Ru, Co, Pt, Fe, Os, Ir, W, Re, Cr, Mo, Mn, Ni, Rh, Pd, Nb, and Ta.

2. A complex as claimed in claim 1 in which said metal is Tc.

3. A complex as claimed in claim 1 in which said metal is Re.

4. A complex as claimed in claim 1, 2 or 3 in which said isonitrile ligand is aliphatic.

5. A complex as claimed in claim 1, 2 or 3 in which said isonitrile ligand is a hydrocarbon isonitrile.

6. A complex as claimed in claim 1, 2 or 3 in which said isonitrile ligand is a saturated hydrocarbon isonitrile.

7. A complex as claimed in claim 1 wherein each coordinate position of said radioactive metal is filled by an isonitrile ligand.

8. A complex as claimed in claim 1 wherein said isonitrile ligand is a monodentate ligand.

9. A complex as claimed in claim 1 wherein said isonitrile ligand is a bidentate ligand.

10. A complex as claimed in claim 1 wherein said isonitrile ligand is a tridentate ligand.

11. A complex as claimed in claim 1 wherein said complex is a cationic lipophilic complex.

12. A complex as claimed in claim 1 wherein said radioactive metal is a radioactive isotope of Tc, Ru, Co, Pt, Fe, Os or Ir.

13. A complex as claimed in claim 1 wherein said radioactive metal is a radioactive isotope of W, Re, Fe or Os.

14. A complex as claimed in claim 1 wherein said radioactive metal is a radioactive isotope of Cr, Mo, Co, Tc, Fe, Mn, W, Ru, Ni, Rh, Ir, Pd, Nb or Ta.

15. An isonitrile complex having the formula:

$$[A((CN)_xR)_yB_zB'_{z'}]^n$$

wherein A is a radionuclide selected from radioactive isotopes of Tc, Ru, Co, Pt, Fe, Os, Ir, W, Re, Cr, Mo, Mn, Ni, Rh, Pd, Ta; $(CN)_xR$ is a monodentate or polydentate isonitrile ligand bonded to the radionuclide through the carbon atom of the CN group; R is an organic radical; B and B' are independently other ligands selected from the class of solvents, halogen groups, and ligands comprising one or more neutral donor atoms capable of forming coordinant bonds with said radionuclide; x and y are each independently, integers from 1 to 8; z and z' are each independently 0 or an integer from 1 to 7; with the proviso that $(xy)+z+z'$ is less than or equal to 8; and n indicates the charge of the complex and can be 0 (neutral), or a positive or negative integer.

16. An isontrile complex having the formula;

$$[A(CNR)_6]^+$$

wherein A is a radionuclide selected from technetium and $^{188}$Re, and R is an organic radical.

17. A cationic lipophilic hexakis t-butylisonitrile complex of technetium.

18. A kit for preparing a coordination complex of an isonitrile ligand and a radionuclide selected from the class consisting of radioactive isotope of Tc, Ru, Co, Pt, Fe, Os, Ir, W, Re, Cr, Mo, Mn, Ni, Rh, Pd, Nb and Ta, said kit comprising a predetermined quantity of said isonitrile ligand and a predetermined quantity of a reducing agent capable of reducing a predetermined quantity of a preselected one of said radionuclides to form said complex.

19. A kit as claimed in claim 18 wherein said isonitrile ligand and said reducing agent are lyophilized.

20. A kit as claimed in claim 18 wherein said lyophilized isonitrile ligand and reducing agent are contained in a sealed, sterilized container.

21. A kit as claimed in claim 18, 19 or 20 wherein said preselected radionuclide is an isotope of Tc.

22. A kit as claimed in claim 18, 19 or 20 wherein said preselected radionuclide is an isotope of Re.

23. A kit for converting a supply of $^{99m}$Tc-pertechnetate to a complex as claimed in claim 1, said kit comprising a supply of an isonitrile and a supply of a reducing agent capable of reducing technetium.

24. A kit as claimed in claim 23 in which said reducing agent is selected from the class consisting of dithionites and stannous salts.

25. A kit as claimed in claim 23 wherein said isonitrile ligand and said reducing agent are lyophilized.

26. A kit as claimed in claim 23 wherein said lyophilized isonitrile ligand and reducing agent are contained in a sealed, sterilized container.

27. A kit as claimed in claim 18 wherein said radioactive metal is radioactive isotope of Tc, Ru, Co, Pt, Fe, Os or Ir.

28. A kit as claimed in claim 18 wherein said radioactive metal is a radioactive isotope of W, Re, Fe, or Os.

29. A kit as claimed in claim 18 wherein said isotope of Cr, Mo, Co, Tc, Fe, Mn, W, Ru, Ni, Rh, Ir, Pd, Nb or Ta.

30. A method for imaging body tissues comprising administering to an animal a radiopharmaceutical composition comprising a coordination complex of an isonitrile ligand and $^{99m}$Tc, and detecting the localization of such complex in the body tissues by a gamma camera.

31. The method of claim 30 wherein said complex is $^{99m}$Tc-hexakis-t-butylisonitrile.

32. The method of claim 30 wherein said complex is $^{99m}$Tc-hexakis-iso-propylisonitrile.

33. A method for detecting vascular emboli in an animal comprising administering to said animal a radiopharmaceutical composition comprising a coordination complex of an isonitrile ligand and $^{99m}$Tc, and detecting the emboli by localization of said complex at said emboli with a gamma camera.

34. The method of claim 33 wherein said complex is $^{99m}$Tc-hexakis-t-butylisonitrile.

35. The method of claim 33 wherein said complex is $^{99m}$Tc-hexakis-iso-propylisonitrile.

36. A method for labeling a cell or liposome comprising incubating said cell or liposome with a coordination complex as claimed in claim 1 in a suitable medium.

* * * * *